United States Patent
Deterre et al.

(10) Patent No.: US 9,511,237 B2
(45) Date of Patent: Dec. 6, 2016

(54) AUTONOMOUS INTRACORPOREAL CAPSULE WITH FREQUENCY CONVERSION ENERGY HARVESTING

(71) Applicant: SORIN CRM SAS, Clamart (FR)

(72) Inventors: Martin Deterre, Paris (FR); Elie Lefeuvre, Montreuil (FR)

(73) Assignee: SORIN CRM SAS, Clamart (FR)

(*) Notice: Subject to any disclaimer, the term of this patent is extended or adjusted under 35 U.S.C. 154(b) by 0 days.

(21) Appl. No.: 14/500,504

(22) Filed: Sep. 29, 2014

(65) Prior Publication Data

US 2015/0094786 A1    Apr. 2, 2015

(30) Foreign Application Priority Data

Oct. 1, 2013  (FR) ...................................... 13 59466

(51) Int. Cl.
*A61N 1/378* (2006.01)
*A61N 1/375* (2006.01)
(Continued)

(52) U.S. Cl.
CPC ............ *A61N 1/3785* (2013.01); *A61N 1/362* (2013.01); *A61N 1/3756* (2013.01); *H02N 1/08* (2013.01);
(Continued)

(58) Field of Classification Search
CPC ............................ A61N 1/3785; A61N 1/3975
See application file for complete search history.

(56) References Cited

U.S. PATENT DOCUMENTS 7,579,757 B2 * 8/2009 Kulah ....................... F03G 7/00
                                                              310/339
7,821,183 B2 * 10/2010 Rastegar ............. H01L 41/1136
                                                              310/339
(Continued)

FOREIGN PATENT DOCUMENTS

DE    102004043002     3/2006
EP    2 520 333        11/2012
(Continued)

OTHER PUBLICATIONS

F. Peano et al, Design and Optimization of a MEMS Electret-Based Capacitive Energy Scavenger, Journal of Microelectromechanical Systems, 14 (3), 429-435, 2005.*
(Continued)

*Primary Examiner* — William Levicky
(74) *Attorney, Agent, or Firm* — Foley & Lardner LLP (57) ABSTRACT

The energy harvester module of the capsule comprises: a primary oscillating structure subjected to an external low-frequency stress; a secondary oscillating structure comprising an elastic element and able to vibrate in high-frequency resonance; and an electrostatic structure with a first electrode coupled to the primary structure and a second electrode coupled to the secondary structure. The electrodes exert a mutual attraction between them driving the secondary structure away from its stable equilibrium position with tensioning of the elastic element, up to a limit beyond which the secondary structure is released by relaxation effect to vibrate at a resonance frequency. A transducer coupled to the secondary structure converts these high frequency vibration movements into electrical energy.

21 Claims, 7 Drawing Sheets (51) Int. Cl.
*A61N 1/362* (2006.01)
*H02N 1/08* (2006.01)
A61N 1/39 (2006.01)
H01L 41/053 (2006.01)
H02N 2/18 (2006.01)

(52) U.S. Cl.
CPC ............ *A61N 1/3975* (2013.01); *H01L 41/053* (2013.01); *H02N 2/18* (2013.01)

(56) References Cited

U.S. PATENT DOCUMENTS

| | | | |
|---|---|---|---|
| 2006/0136004 A1 | 6/2006 | Cowan et al. | |
| 2007/0088397 A1 | 4/2007 | Jacobson | |
| 2007/0167988 A1* | 7/2007 | Cernasov | H02N 11/002 607/35 |
| 2007/0276444 A1 | 11/2007 | Gelbart et al. | |
| 2011/0140577 A1* | 6/2011 | Galchev | H02N 2/186 310/339 |
| 2012/0283807 A1* | 11/2012 | Deterre | A61N 1/3975 607/116 |

FOREIGN PATENT DOCUMENTS

| | | |
|---|---|---|
| EP | 2 638 930 | 9/2013 |
| EP | 2 639 845 | 9/2013 |
| WO | WO-2007/047681 A2 | 4/2007 |

OTHER PUBLICATIONS

Foreign Search Report for French Patent Application No. FR 1359466, dated Dec. 12, 2013, 2 pages.

* cited by examiner

AUTONOMOUS INTRACORPOREAL CAPSULE WITH FREQUENCY CONVERSION ENERGY HARVESTING

CROSS-REFERENCE TO RELATED APPLICATION

This application claims the benefit of and priority to French Patent Application No. 1359466, filed Oct. 1, 2013. French Patent Application No. 1359466 is hereby incorporated by reference in its entirety.

BACKGROUND

The invention is related to the field of the "medical devices" as defined by the directive 93/42/CE of Jun. 14, 1993 of the European Communities, and notably the "active implantable medical devices" as defined by the directive 90/385/CEE of Jun. 20, 1990 of the European Communities. This definition in particular includes the implants that continuously monitor the cardiac rhythm and deliver if necessary to the heart electrical pulses of stimulation, cardiac resynchronization, cardioversion and/or defibrillation in case of a rhythm disorder detected by the device. It also includes neurological devices, cochlear implants, etc., as well as devices for pH measurement or devices for intracorporeal impedance measurement (such as the measure of the transpulmonary impedance or of the intracardiac impedance).

The invention relates more particularly to those of these devices that implement autonomous implanted capsules and are free from any physical connection to a main implanted (such as the can of a stimulation pulse generator).

These autonomous capsules are called for this reason "leadless capsules" to distinguish them from the electrodes or sensors placed at the distal end of a lead, this lead being traversed throughout its length by one or more conductors connecting by galvanic liaison the electrode or the sensor to a generator connected at the opposite, proximal end, of the lead. Such leadless capsules are, for example, described in U.S. 2007/0088397 A1 and WO 2007/047681 A2 (Nanostim, Inc.) or in U.S. 2006/0136004 A1 (EBR Systems, Inc.).

These leadless capsules can be epicardial capsules, fixed to the outer wall of the heart, or endocardial capsules, fixed to the inside wall of a ventricular or atrial cavity, by a protruding anchoring helical screw, axially extending the body of the capsule and designed to penetrate the heart tissue by screwing to the implantation site. The invention is nevertheless not limited to a particular type of capsule, and is equally applicable to any type of leadless capsule, regardless of its functional purpose.

A leadless capsule includes various electronic circuits, sensors, etc., and a transmitter/receiver for wireless communication for remote data exchange. The signal processing inside the capsule and its remote transmission requires a non-negligible energy compared to the energy resources this capsule can store. However, due to its autonomous nature, the capsule can only use its own resources, such as an energy harvester circuit (by the movement of the capsule), associated with an integrated small buffer battery.

A first type of energy harvester uses a transducer coupled to an inertial mechanism including a mobile mass, called "seismic mass", oscillating in the capsule according to the movements of the latter, which is subject to forces due to movements of the wall the organ of the patient and to fluid forces from the surrounding medium. The recovered power mainly depends on the excitation frequency of the seismic mass, of the amplitude of the movement and of the value of mass. However, in the case of the environment of the human body, the excitations from the acceleration of the body or organs do not have stable specific frequencies for which the harvesting may be optimized to produce a mechanism resonance. Thus, it is not possible to benefit from a mechanical amplification which would increase the amplitude and allow harvesting of a maximum of inertia energy. Furthermore, the excitation frequencies involved are very low, of the order of 0.5 to 10 Hz for typical pulse frequency of blood flow and 15 to 40 Hz for the movements of the heart walls, which limits performance of the harvester. Finally, the mass value of the seismic mass must remain very low, for fulfilling miniaturization requirements.

Another, non-inertial, type of energy harvester uses variations of the pressure of the fluid surrounding capsule (typically blood medium) to cyclically deform or move a flexible membrane or a bellows coupled to a transducer. The energy that can be harvested depends mainly on the magnitude of the cyclic movement of the diaphragm or bellows operated by the surrounding fluid (which amplitude is necessarily limited for reasons of mechanical reliability), on the frequency of the cyclic movement and on the area of the moving surface (necessarily limited for obvious reasons of miniaturization of the capsule). Again, the pressure variations occur at the heart rate, of the order of 1 to 3 Hz, and therefore only allow applying low frequency to the transducer, thus imposing a limitation of the performance of the energy harvester.

One aspect of the present invention may overcome these limitations by proposing a new type of energy harvester provided with a mechanism increasing the excitation frequency of the transducer, so as to benefit, for a single cycle of external stress, from a plurality of transduction cycles for converting the procured mechanical energy.

On this aspect, U.S. 2011/0140577 A1 describes a ciliated energy harvesting device including two suspended magnets, mounted face-to-face and in opposite poles and each carried by an elastic membrane, together with an inertial mass bearing a third intermediate magnet. The comings and goings of the inertial mass causes successive coupling/decoupling of the suspended magnets at a frequency higher than that of the oscillation of the inertial mass. The oscillation energy of each suspended magnet is harvested by a fixed coil within which the magnet oscillates. While this structure improves the efficiency of energy harvesting, nevertheless it retains the disadvantages described above relating to the dual presence, by nature essential, of a seismic mass and of magnetic means.

Another aspect of the invention may provide such a mechanism that can be used both with a seismic mass inertial harvester, biased by external vibrations and movements of the surrounding environment and with a non-inertial harvester with a membrane or bellows biased by cyclical variations in fluid pressure that surrounds the capsule.

Yet another aspect of the invention may provide such a mechanism that does not implement any magnetic element that would create a risk during MRI or any repetitive shock or mechanical contact which would result in the long term mechanical reliability problems.

SUMMARY

The present invention may implement two moving elements, namely:

A first structure, hereinafter "primary oscillating structure" submitted to a low frequency external stress that can be a force directly applied e.g. from pressure changes cyclically moving a membrane or a bellows, or indirectly by a seismic mass integral with this structure, this structure moving at the same low frequency; and A second structure, hereinafter "secondary oscillating structure", vibrant at a higher frequency, typically with a resonance effect and coupled to the transducer of the energy harvester.

To achieve this frequency conversion, both primary and secondary structures are coupled together by a mechanism achieving a "pull-release" function, creating a relaxation phenomenon. This coupling between the two oscillating structures is made, typically, by a coupling structure operating by electrostatic interaction, and therefore without any rubbing or impact magnetic or mechanical element.

More specifically, the invention proposes an autonomous intracorporeal capsule having a body and, inside said body, electronic circuits and a module for energy harvesting for the power supply these electronic circuits. The energy harvesting module includes a transducer adapted to convert into electrical energy a cyclic external physical stress applied to the body of the capsule, and resulting from pressure variations in the environment surrounding the capsule and/or from movements of a wall in which the capsule is anchored.

According to an embodiment of the invention, the energy harvesting module includes:

A primary oscillating structure subjected to external cyclic stress, this primary oscillating structure being adapted to be moved alternately in one direction and in the other at the frequency of the external cyclic stress;

A secondary oscillating structure not subject to the cyclic external stress, this oscillating structure including a secondary deformable elastic member and being adapted to freely vibrate at a resonant eigenfrequency higher than the frequency of the external cyclic stress; and An electrostatic structure including a first capacitor electrode coupled to the primary oscillating structure or to the body of the capsule, and a second capacitor electrode coupled to the secondary oscillating structure.

The first and second electrodes are configured so that, under the effect of the external cyclic stress applied to the primary oscillating structure, they operate together under the effect of electrostatic interactions by a mutual attraction force driving the secondary oscillating structure away from its stable equilibrium position and with a tensioning of the deformable elastic element. The secondary oscillating structure is thus driven to a limit so that the tension exerted by the deformable resilient element exceeds the mutual attraction force of the electrodes, such that the secondary oscillating structure is then released by relaxation effect to vibrate freely to said resonance eigenfrequency. Finally, the transducer is coupled to the secondary oscillating structure, to convert into electrical energy the vibration movements thereof at said resonance eigenfrequency.

The transducer can be of the electrostatic type. It then includes conversion electrodes forming a capacitor, one of these conversion electrodes being cyclically driven by the secondary oscillating structure, and the transducer operating by cyclic variations of the surfaces vis-à-vis and/or of the dielectric interval of the conversion electrodes with correlative variation in the capacitance of the capacitor. The conversion electrodes may include the first and second electrodes of the electrostatic structure. The transducer can also be of the piezoelectric type, including a deformable piezoelectric element configured to be cyclically constrained by the secondary oscillating structure. The transducer may also be of the electromagnetic type, including a mobile magnetic element or a mobile coil configured to be cyclically driven by the secondary oscillating structure.

In a first embodiment, the primary oscillating structure includes an inertial mass coupled to the body of the capsule by a resilient suspension adapted to be cyclically stressed under the effect of the movement of the capsule into the surrounding medium. The primary oscillating structure can in particular be coupled to a deformable surface outer of the capsule body, adapted to be cyclically stressed under the effect of pressure changes in the medium surrounding the capsule.

In a second embodiment, the primary and secondary oscillating structures are coupled together by the electrostatic structure. The secondary oscillating structure can be coupled to the body of the capsule by the resilient deformable element, and the first electrode of the electrostatic structure can be connected to the primary oscillating structure, the second electrode of the electrostatic structure being connected to the secondary oscillating structure.

In a third embodiment, the primary and secondary oscillating structures are coupled together by the deformable elastic element. The first electrode of the electrostatic structure can be connected to the capsule body, the second electrode of the electrostatic structure being connected to the secondary oscillating structure.

In a fourth embodiment, the first and second electrodes of the electrostatic structure are formed as respective fingers of nested comb(s) and counter-comb(s). The fingers of one of the at least first and second electrodes of the electrostatic structure are then resiliently deformable fingers, together forming the deformable elastic element of the secondary oscillating structure. The distal ends of these fingers can be joined together by a rigid coupling.

According to another embodiment, there is a method for harvesting energy in an implantable device. The method includes the steps of receiving an external force that causes a first oscillating structure to move in the direction of a second oscillating structure and engaging the second oscillating structure with the first oscillating structure via the movement of the first oscillating structure towards the second oscillating structure. When engaged, the second oscillating structure is pulled away from an equilibrium position to create tension in a deformable elastic element coupled to the second oscillating structure. Release between the second oscillating structure and the first oscillating structure occurs when the tension in the deformable elastic element exceeds a tension limit. Energy is then harvested from the oscillations of the second oscillating structure (e.g., after it is released from the first oscillating structure and vibrates at a resonant frequency).

BRIEF DESCRIPTION OF THE FIGURES

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

It will first be described with reference to FIGS. 1 to 7, the basic structure of a capsule and a leadless embodiment of an energy harvester for such a capsule, according to prior art.

Figures 1, 2, 3, 4:
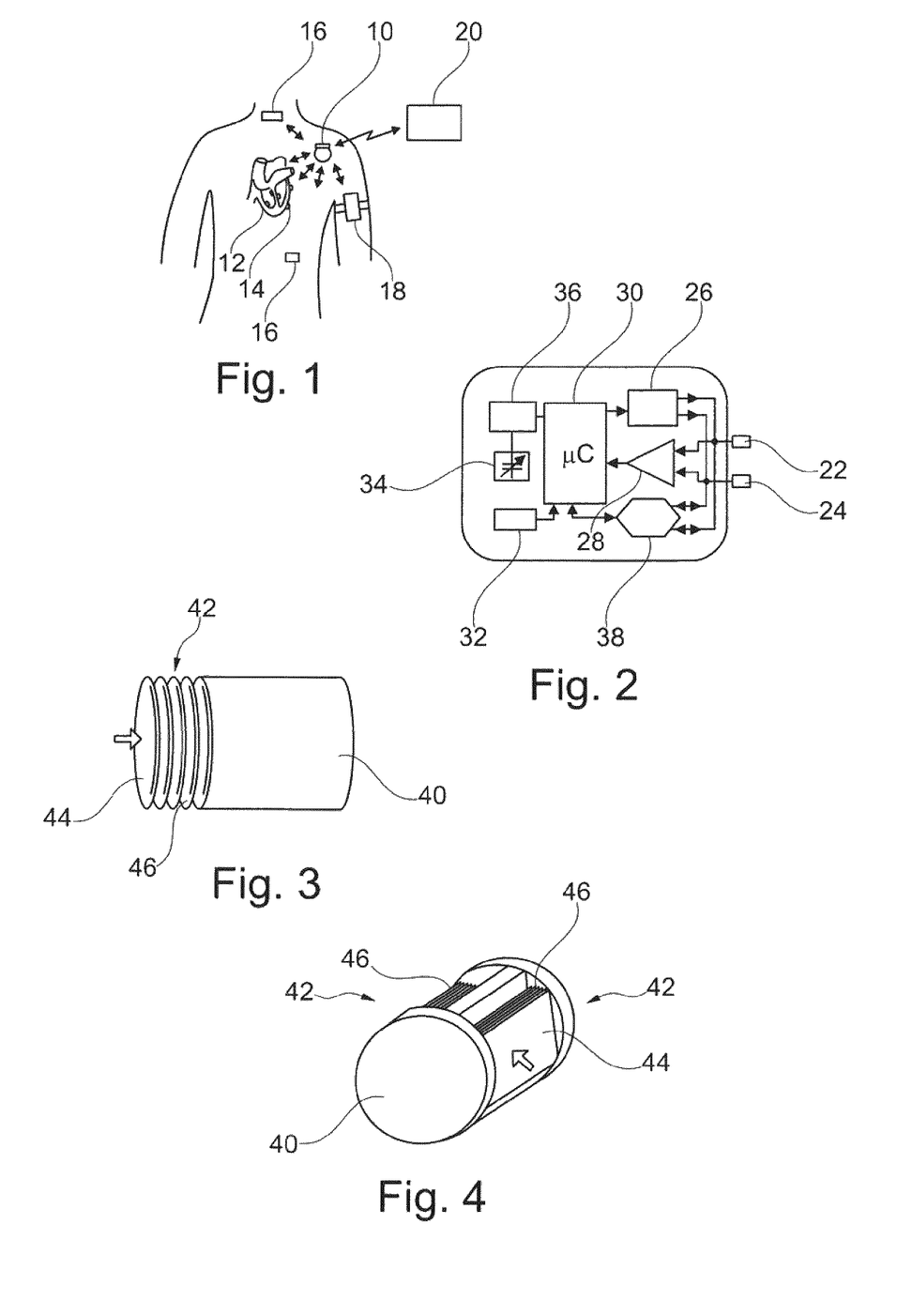
FIG. 1 schematically illustrates a set of medical devices including leadless capsules, implanted within the body of a patient.
FIG. 2 is a functional block diagram showing the various stages constituting a leadless capsule.
FIGS. 3 and 4 illustrate two possible embodiments of a leadless capsule body with harvesting methods of the pressure variations of the surrounding fluid.

In FIG. 1 a set of medical devices implanted within the body of a patient is illustrated. The patient is implanted for example with an implant 10 such as an implantable defibrillator/pacemaker/resynchronizer or a subcutaneous defibrillator or a long-term event recorder. This implantable device 10 is the master device of a network including a plurality of slave devices 12 to 18, which may include intracardiac (12) or epicardial (14) capsules located directly on the patient's heart, other devices such as myopotential sensors or neurological stimulation devices, and optionally an external device 18 disposed on an armband and provided with electrodes in contact with the skin. The device 10 can also be used as a gateway with the external environment to communicate with an external peripheral device 20 such as a programmer or a data remote transmission device with which it communicates by telemetry.

FIG. 2 schematically illustrates the different internal autonomous circuits of the implanted capsules 12-16 shown in FIG. 1.

The capsule includes for example a pair of electrodes 22, 24 connected to a stimulation pulse generator circuit 26 (for an active capsule incorporating this feature) and/or a detection circuit 28 for the collection of depolarization potential collected between electrodes 22 and 24. A central circuit 30 includes all of the electronics for controlling the various functions of the capsule, for storing the collected signals, etc. It includes a microcontroller and an oscillator generating the clock signals required for the operation of the microcontroller and for the communication. It may also contain an analog/digital converter and a digital storage memory. The capsule may also be provided with a sensor 32 such as an acceleration sensor, a pressure sensor, an hemodynamic sensor, a temperature sensor, an oxygen saturation sensor, etc. The capsule includes an energy harvesting module 34 powering all the circuits via an energy power management stage 36. Electrodes 22 and 24 are also connected to a transmission/reception circuit of pulses 38 used for wireless communication with the master device or other capsules.

The present invention relates particularly to the energy harvesting module 34. The purpose is to harvest the energy contained in the mechanical forces to which the capsule is subjected.

Two special cases of external stresses can be considered:

Harvesting of vibration energy, also referred to as inertial energy, by a seismic mass subjected to the acceleration efforts and which produces a force equal to the product of this acceleration by the moving mass; or Harvesting of cardiac pressure variations by providing a body part of the capsule deformable under the influence of these pressure fluctuations. The force generated is proportional to the product of the amplitude of the pressure variations by the surface of the deformable element.

In either case, the frequency of the cyclic stresses is, in the cardiac environment, in ranges of the order of 1 to 3 Hz (frequency of the heartbeat) and also around 15 to 20 Hz, for the vibrations of a seismic mass, and in the range 1-3 Hz of the heartbeat for the changes in blood pressure.

FIGS. 3-7 illustrate various embodiments of existing devices suitable for the harvesting of pressure forces by a capsule, such as those disclosed in, for example, EP 2520333 A1 (Sorin CRM). However, the aspects of the present invention discussed herein are not limited to use in devices such as those shown in the figures or described in EP 2520333, and may also apply to, for example, energy harvesting systems implementing a seismic mass.

To take into account pressure variations, the capsule is formed, as shown in FIGS. 3 and 4, with a body 40 provided with one or more deformable elements 42 biased at the rhythm of the pressure variations of the fluid that surrounds the capsule, typically changes in blood pressure. The deformable element 42 includes a rigid surface 44 on which the pressure variations are exerted, and is connected to the body 40 by a deformable bellows 46. In the example of FIG. 3, this surface/bellows set 44/46 is disposed on an axial end side of the capsule 40, while in the example of FIG. 4 there are provided two surface/bellows sets 44/46 disposed on lateral sides of the body 40 of the capsule, the rigid surfaces 44 being parallel to each other and to the main axis of the capsule.

Figure 5:
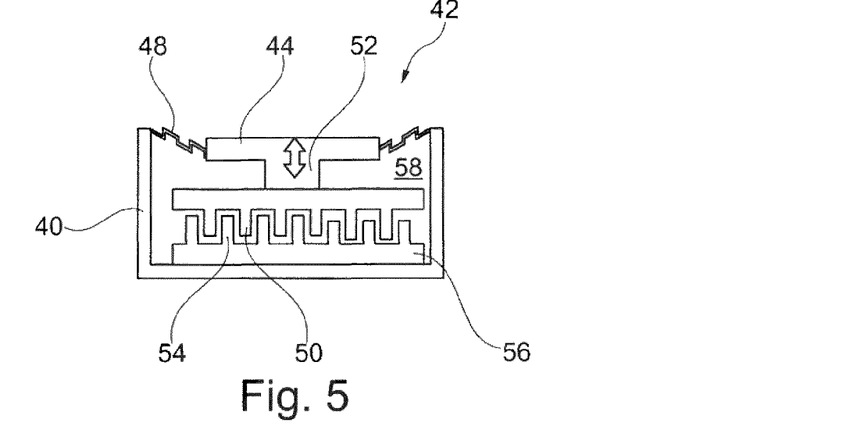
FIGS. 5-7 show variants of the internal structure of a known leadless capsule with harvesting methods of the pressure variations and an electrostatic transducer.
Figure 6:
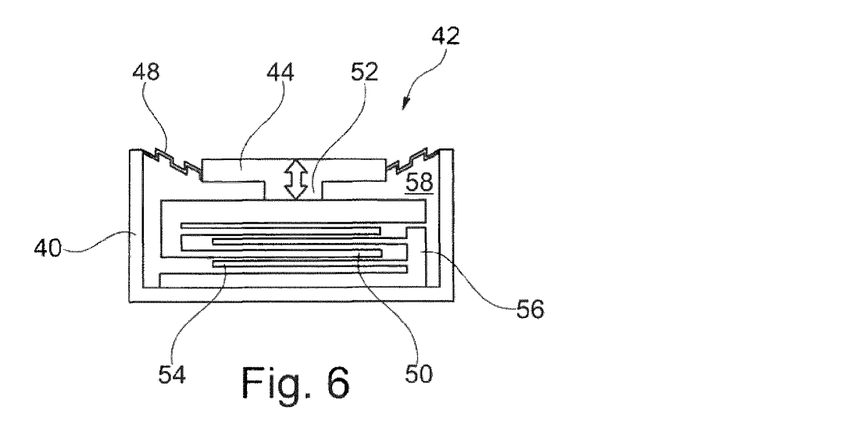
Figure 7:
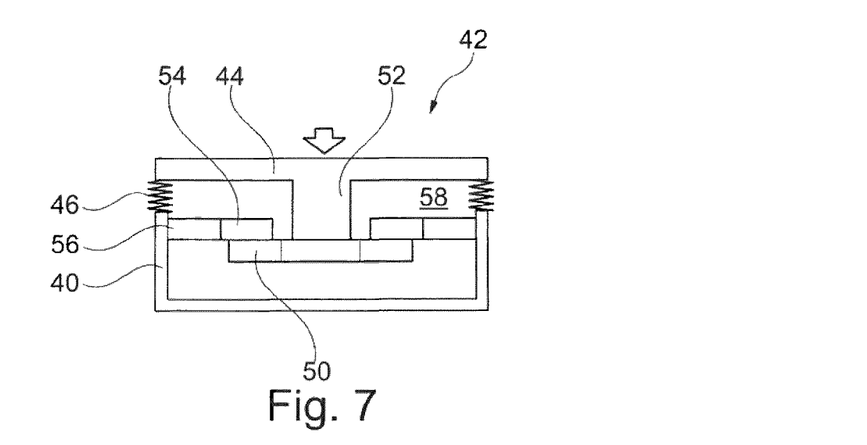

FIGS. 5-7 illustrate various possible structures of an electrostatic transducer for energy harvesting of the pressure variations by the deformable element 42. This transduction mode is, however, not limiting the present invention which, as will be seen below, may also implement a transducer operating according to another, for example an electromagnetic or a piezoelectric, principle.

In FIGS. 5-7, the mobile surface 44 is coupled to the body 40 by a resilient connection element 48 (FIGS. 5 and 6) or by a bellows 46 (FIG. 7). This mobile surface 44 is connected to a series of first conversion electrodes 50 via a coupling element 52. These electrodes are preferably configured in the form of combs, for example, made by conventional photoetching techniques. The device further includes second conversion electrodes 54 provided in the form of counter-combs interdigitated with the electrodes combs 50 and connected to the body 40 by a peripheral support 56. The assembly formed by these electrodes 50, 54 is enclosed in the sealed volume 58 formed by the body 40 enclosed by the deformable element 42.

This provides a transducer which can be modelled by a variable capacitor including:

A first, suspended, conversion electrode constituted by the combs 50 which are mechanically and electrically connected together and to the mobile surface via the element 52;

A second, fixed, conversion electrode constituted of the counter-combs 54 which are mechanically and electrically connected together and to the body 40 via the support 56; and A dielectric gap, defined between the two electrodes.

In the configuration of FIG. 5, in case of depression of the mobile surface 44 the gap and the overlap in the plane of the combs remain constant, but the vertical overlap changes during movement. In the case of FIG. 6, the electrodes are configured with a variable dielectric interval, while in the case of FIG. 7, the electrodes are configured with overlapping in the plane, the rest of the structure being identical to what has been shown in FIG. 5. But in all cases, there is an element whose capacitance cyclically varies at the pace of movement of the mobile surface 44 and therefore the variations of the blood pressure of the surrounding medium.

If the capacitor has been charged in advance, a diminution of capacity produces excess energy that can be discharged through appropriate circuitry to a storage module, and vice versa. For each cardiac cycle an amount of energy can be recovered and that will be sufficient in the long run to ensure continuous operation of the electronic circuits of the capsule, without additional energy input.

FIGS. 8-21 depict various aspects and embodiments of the invention to substantially increase the conversion efficiency of devices such as those described above.

Figure 8:
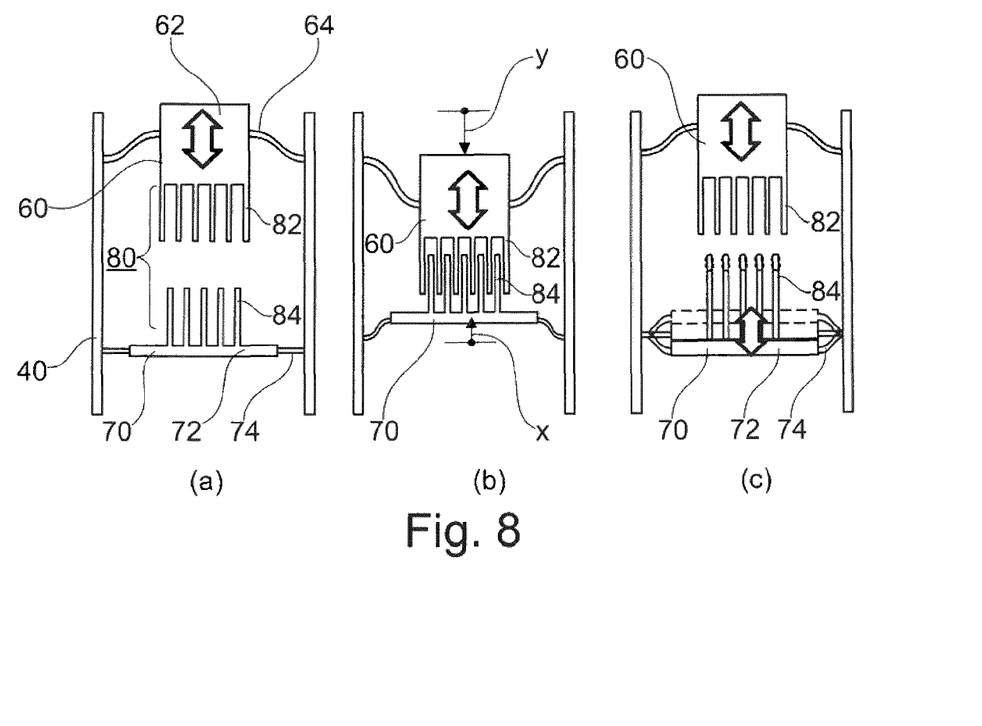
FIG. 8 illustrates the principle of frequency conversion according to the invention, by implementing a dual oscillating structure and a relaxation electrostatic coupling.

FIG. 8 shows the conversion principle according to the invention. Essentially, it involves using electrostatic forces involved in the application of a voltage of an electrical charge between two parts of a variable capacitor to cause a phenomenon of "pull-release" of a structure for transduction of a mechanical energy into electrical energy. Specifically, this structure includes two mobile parts, hereinafter referred to as "primary oscillating structure" (designated 60 in the figures) and "secondary oscillating structure" (designated 70 in the figures, the numerals being maintained in all figures to designate in different embodiments, functionally similar structures).

The primary structure 60 is subjected to low frequency external stress such as a direct force or, as in the embodiment of FIG. 8, the vibration of seismic mass 62 mounted on a resilient suspension 64 connected to the body 40 of the capsule. The secondary structure 70 includes a mobile element 72 and an elastically deformable element 74, which is in the embodiment of FIG. 8 a suspension connecting the mobile part 70 to the body 40 of the capsule. The mass of the mobile element 72 and the elasticity of the suspension 74 define for the secondary structure 70 a self-resonant eigenfrequency, which is typically substantially higher than the frequency at which the primary structure 60 is biased.

The two oscillating structures 60, 70 are coupled together by an electrostatic structure referenced 80, including two respective series of electrodes 82, 84 whose relative displacement has the effect of varying the capacitance of the capacitor formed by the respective electrodes. The following various possible configurations of the electrodes 82, 84 of the electrostatic structure 80 are exhibited hereafter, the same numeral references 80, 82 and 84 being retained in the different figures to denote similarly functioning elements.

In the embodiment of FIG. 8, the electrodes 82 are integral with the primary oscillating structure 60, and the electrodes 84 are integral with the secondary oscillating structure 70. The dynamic behaviour of this structure can be explained with reference to FIGS. 8 and 9.

Figure 9:
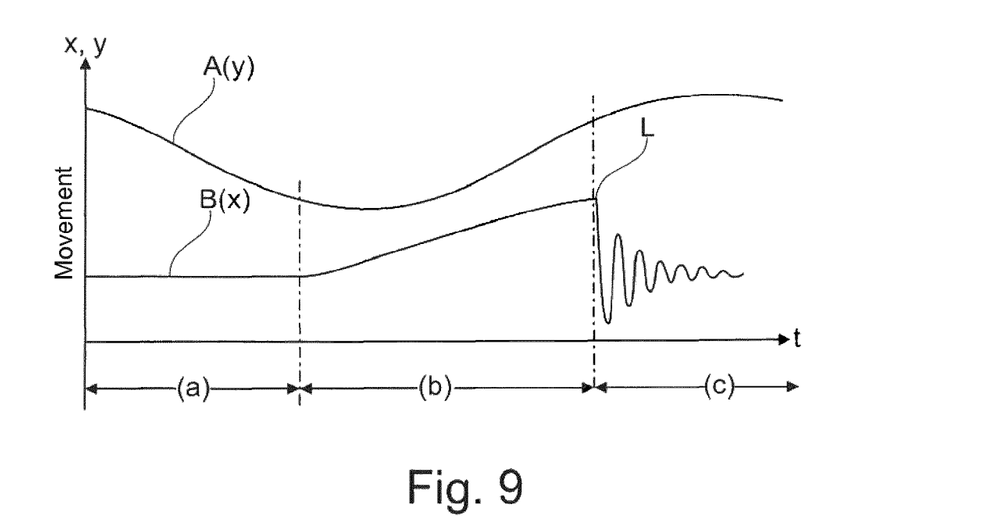
FIG. 9 illustrates the respective movements of the two oscillating structures of the configuration of FIG. 8, during a cycle of mechanical stress in the primary structure.

The primary structure 60, during its movement (at the cyclic external stress frequency, corresponding to curve A in FIG. 9) will end up facing the secondary structure 70 with progressive overlapping of electrodes 82, 84 (passage from state (a) to state (b) in FIG. 8). If a voltage or an electrical charge is applied between the electrodes 82, 84 facing each other, an electrostatic interaction, typically a pull, takes place between these electrodes. This interaction will effectively attract the secondary structure 70 to the primary structure 60, as shown by curve B in FIG. 9, which represents the displacement of the structure 70. The resulting attraction of the electrostatic interaction corresponds to the displacement in the area (b) of FIG. 9.

The electrostatic attraction force between the two structures 60 and 70 will pass through a maximum, strong enough for the secondary structure 70 driven by the primary structure 60 ("pull" step). But the displacement of the secondary structure 70 is more limited. Once a boundary L is reached, the stiffness of the suspension 74 will separate the two structures ("release" step). No longer attracted by the primary structure 60 which moves away, the secondary structure 70, released from a stretched state of the suspension 74, will enter into free vibration at its natural resonance eigenfrequency, as shown in (c) in FIGS. 8 and 9.

The vibrations of the secondary structure 70, being the one that provides the transduction, will cause many transduction cycles before the primary structure returns in the action area of the secondary structure, to perform a new pull-release cycle-to-cycle. In order to achieve the desired effect of "pull-release", the electrostatic attraction should result in a displacement of the secondary structure of the same order of magnitude as the characteristic dimensions of the structure.

Hereinafter, the expression "of the same order of magnitude" should be understood in its specific meaning conventionally used in physics, that is to say in a ratio of 0.1 to 10. More specifically, the electrostatic attraction force $f_e$ (expressed in N) between the fingers forming the electrodes is:

$$f_e = \in *L*V^2/g,$$

$\in$ being the permittivity of the gas (typically air or vacuum) between the fingers forming the capacitor electrodes, L being the length of the face-to-face surface of the electrodes in the dimension perpendicular to the coupling movement, V being the voltage applied between the electrodes, and g being the gap between these electrodes.

If the deformable element supporting the secondary structure has a stiffness k (N/m), then the spring force $f_r$ under deformation x is (N):

$$f_r = k*x.$$

Thus, in quasi-static equilibrium during pull movement, the displacement is:

$$x = \in *L*V^2/(g*k).$$

If h is a characteristic dimension of the fingers, such as for example their thickness, then for a displacement x of the same order of magnitude as h, a stiffness k of at least the same order of magnitude as $\in*L*V^2/(g*h)$ is required.

In contrast, the deformable element should not be too soft, that is to say, with k too low, otherwise there will never be a "release", the stiffness being never significant enough to leave the structure of the electrostatic attraction and for producing relaxation around the equilibrium position. That is why it is necessary that the stiffness k of the system is equal (to an order of magnitude) to $\in*L*V^2/(g*h)$.

From the mechanical point of view, if each finger is approximated to a beam of length L, of thickness h (in the direction of the bending direction) and of width w (transverse to the direction of bending), the value of the electrostatic force can be expressed as a linear force (expressed in N/m) of a value $f_e=\in*V^2/g$, acting along the fingers.

Using the laws of mechanics, the finger rigidity $f_r$ can be expressed by unit length (N/m), when the latter undergoes bending of an amplitude x, at the fingertip, by:

$$f_r = \frac{2}{3}*E*x*h^3*w/L^4,$$

wherein E is the Young's modulus of the material of the finger. The phenomenon of bending of the fingers, and therefore of frequency conversion, becomes significant when $f_e$ becomes substantially greater than $f_r$, for a deflection x of the order of magnitude of h.

Thus, to produce the characteristic effects of the present invention, the fingers should be dimensioned such that the value of $\in*V^2/g$ is equal to that of $E*x*h^3*w/L^4$, to an order of magnitude.

In addition, to avoid instabilities of the fingers in the plane, namely the fact that they can deflect in the plane by reducing the gap (pull-in effect), the fingers preferably have a width w greater than their thickness h to make them rigid in the plane, compared with their desired off-plane flexibility.

The multiplication of the operating frequency of the transducer (at the natural resonant eigenfrequency of the secondary oscillating structure 70 and not at the low frequency of the cyclic external stresses) has the effect of substantially increasing the conversion efficiency of the transducers transforming mechanical energy of forces applied to the capsule into electrical energy. Indeed, if at each transduction cycle the transducer converts a given fraction of mechanical energy into electrical energy, and if the transduction frequency is a multiple of the excitation frequency, then the transduction efficiency by excitation cycle is multiplied accordingly.

Figure 10:
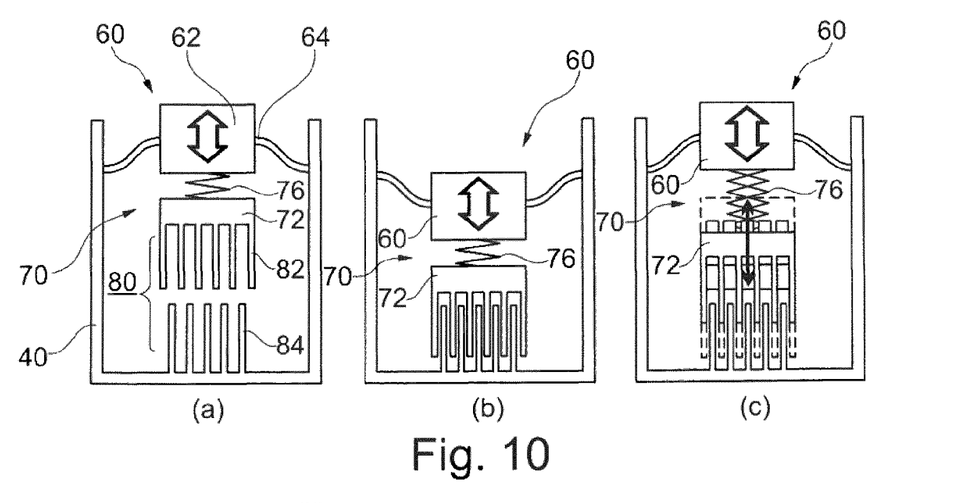
FIG. 10 is the counterpart of FIG. 8, for an alternative embodiment for a set of fixed electrodes integral with the capsule body.

The system described above may be implemented in various possible embodiments. In the case of FIG. 10, the deformable elastic element that defines the resonance frequency of the secondary structure 70 is no longer, as in FIG. 8, a suspension coupling this structure to the body of the capsule, but a spring 76 connecting the seismic mass 62 of the primary structure 60 to the mobile portion 72 of the secondary structure 70. Electrodes 84 are always carried by the mobile portion 72 of the secondary structure 70; the electrodes 82 on the other hand are fixed electrodes integral to the body 40 of the capsule.

As illustrated in (a) in FIG. 10, the system combines the primary structure 60 and the secondary structure 70 and initially has a uniform motion induced by low-frequency excitation of the primary structure 60 by the external stress. When this structure is within the field of electrostatic attraction of the fixed structure constituted by the electrodes 82, as shown in step (b) of FIG. 10, then the secondary structure 70 will experience, in addition to the restoring force connecting it to the primary structure 60 (due to the spring 76), an electrostatic attraction force which will cause a separation of the movement of the two primary and secondary structures 60 and 70 ("pull" step). As with the embodiment of FIG. 8, when the primary structure 60, in its slow oscillation movement, begins to move away, the rigidity between the two structures takes precedence ("release" step) and the secondary structure 70 suddenly goes out of the attraction field of the fixed electrostatic structure 82, causing the high-frequency vibration with multiplication of transduction cycles as shown in (c) in FIG. 10.

Figures 11, 12, 13:
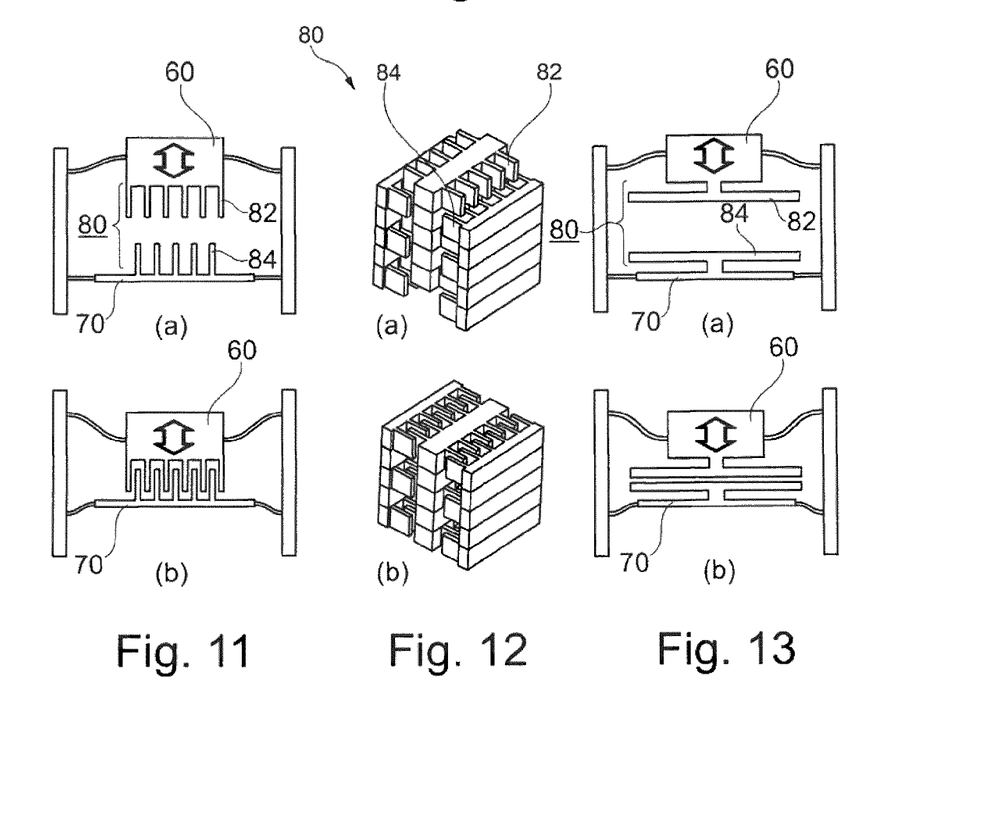
FIGS. 11-13 illustrate various examples of possible electrostatic configurations between two oscillating structures.

FIGS. 11, 12 and 13 show three possible examples of electrostatic structure, wherein the configuration of the facing surfaces advantageously includes surfaces wide separated by a small gap, so as to create a high capacity and therefore a large variation in the capacity during the relative movement of the electrodes. It is thus possible in particular to have interdigitated combs to maximize the facing surfaces, with a variable overlap, outside the plane (FIG. 11) or in the plane (FIG. 12). The capacitance change may also result from a variation of air gap between the facing surfaces of the electrodes (FIG. 13).

Figure 14:
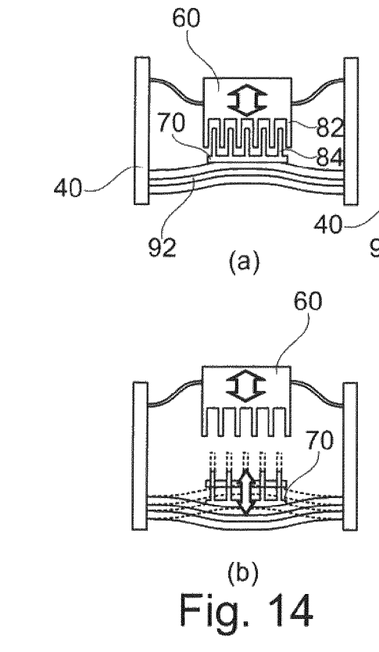
FIGS. 14-16 illustrate various possible examples of transducers to associate to the secondary oscillating structure of the mechanism of the invention.
Figure 15:
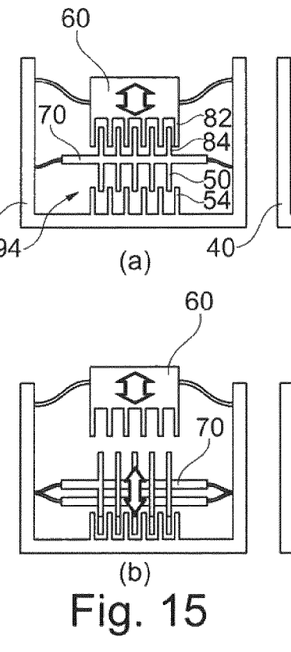
Figure 16:
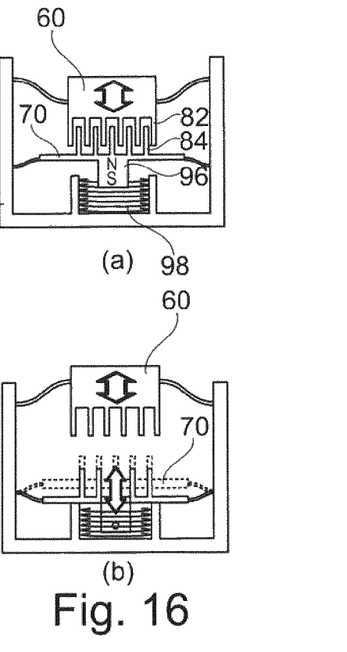

Transduction in electrical energy of the movement of the secondary structure 70 may be made according to various methods, as schematically illustrated in FIGS. 14-16.

FIG. 14 illustrates the case of a piezoelectric transducer, for example by providing a part of the suspension of the secondary structure 70 carrying the electrodes 84 with a piezoelectric material 92, which is subjected to stresses during the movement and therefore will generate charges on these electrodes. These electrodes are situated on either side of the piezoelectric material 92 and are connected to an electronic control circuit, typically a current rectifier and a filtering capacitor.

FIG. 15 illustrates the case of an electrostatic transducer, which in the illustrated embodiment includes electrodes 50, 54 (functionally similar to those described above in connection with FIGS. 5-7) forming a capacitor 94 whose capacity varies at high frequency. The terminals of the capacitor 94 are connected to an electronic circuit performing at each capacity variation cycle a charging and discharging of the capacitor, so as to generate a positive electrical power. Note that in FIG. 15 a transducer 94 is described including a set of electrodes 50, 54 separate from the electrodes 82, 84 of the electrostatic structure 80 performing the frequency conversion according to the invention. It is however possible, and even advantageous, to implement the electric power transduction through the variable capacitor formed by the electrodes 82, 84 of the electrostatic structure 80 in the various embodiments described herein, in other words, using these electrodes 82, 84 not only for the coupling of the oscillating structures and the conversion of the oscillation frequency (mechanical function) but also to ensure the conversion of the movement into electrical energy (mechanic-electric transduction function).

FIG. 16 illustrates the case of an electromagnetic transducer, wherein the mobile part of the secondary structure 70 supports a mobile permanent magnet 96 within a stationary coil 98 secured to the body 40 (or vice versa) so as to generate a high frequency variable magnetic field.

These various types of transducers are not limiting, and other techniques may also be used, for example based on magnetostrictive transducers, using electroactive polymers, etc.

Figure 17:
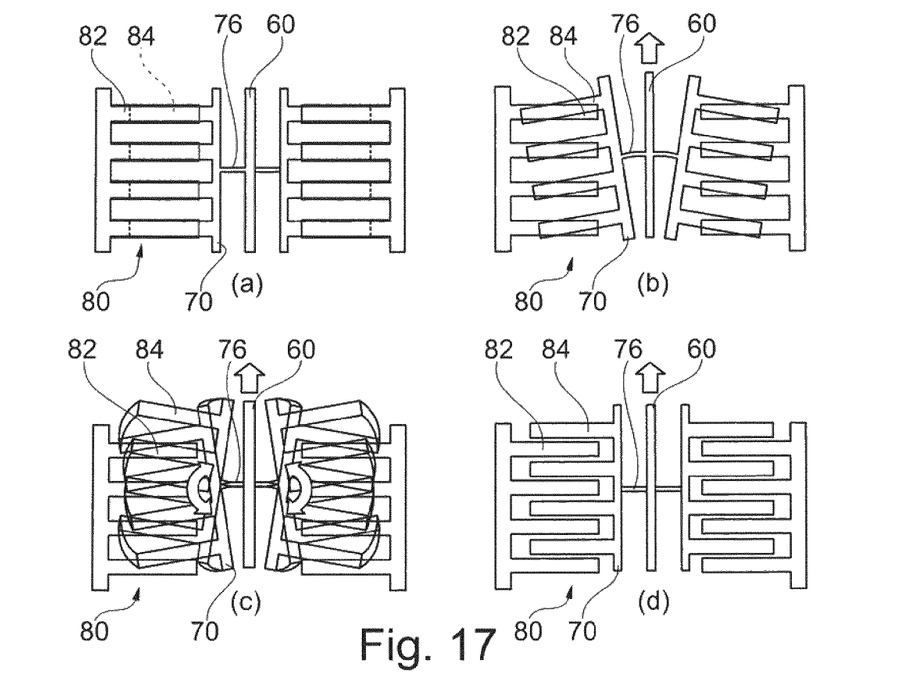
FIG. 17 illustrates a possible implementation of the system of frequency conversion according to the invention, using the rotation of rigid electrostatic fingers with respect to a central structure forming the primary oscillating structure.

FIG. 17 illustrates another possible embodiment of the frequency conversion system according to the invention, by implementing a rotation of the electrodes 84 relative to the electrodes 82, which are fixed and rigid.

The states (a) to (d) illustrate the successive phases of deformation and of relative displacements of the different elements of the set. At rest (condition (a)), combs and combs-against of respective electrodes 82, 84 are still and face to face. The central element 60 of the assembly makes up the primary structure, which is subjected to external forces, via a seismic mass in the case of an inertial harvesting, or via a mobile surface with a bellows in the case of pressure change harvesting, and therefore its movement is dictated by this low-frequency cyclic external stress. At the start of movement (state (b) in FIG. 17), the central portion 60 begins to shift; however, the combs 84 are subject to electrostatic attraction of the counter-combs 82, which opposes the movement. In this way, the flexible element 76 connecting the central element 60 forces the combs and counter-combs 82, 84 to remain facing each other to the maximum ("pull" step).

As the movement grows, the stiffness of the flexible element 76 outweighs the electrostatic attraction, and combs will be suddenly be released ("release" step corresponding to the state (c) in FIG. 17). These combs 84 will then enter a phase of high frequency free vibration, this frequency which can reach hundreds or thousands of hertz being defined by the very low mass of combs 84 and the stiffness of the flexible element 76. During this vibration, the capacitance between the combs 84 and the counter-combs 82 will also vary at high frequency, and several charge/discharge cycles of the capacitor will be performed, greatly increasing the energy extracted per time unit.

Figure 18:
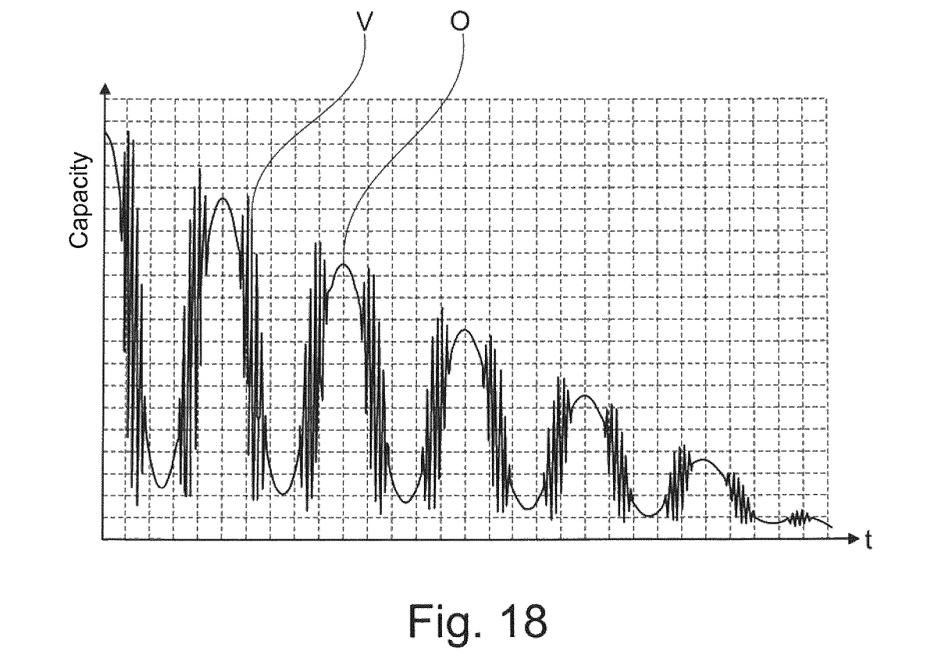
FIG. 18 is a graph showing variations in capacity over time of a structure such as that of FIG. 17.
Figure 19:
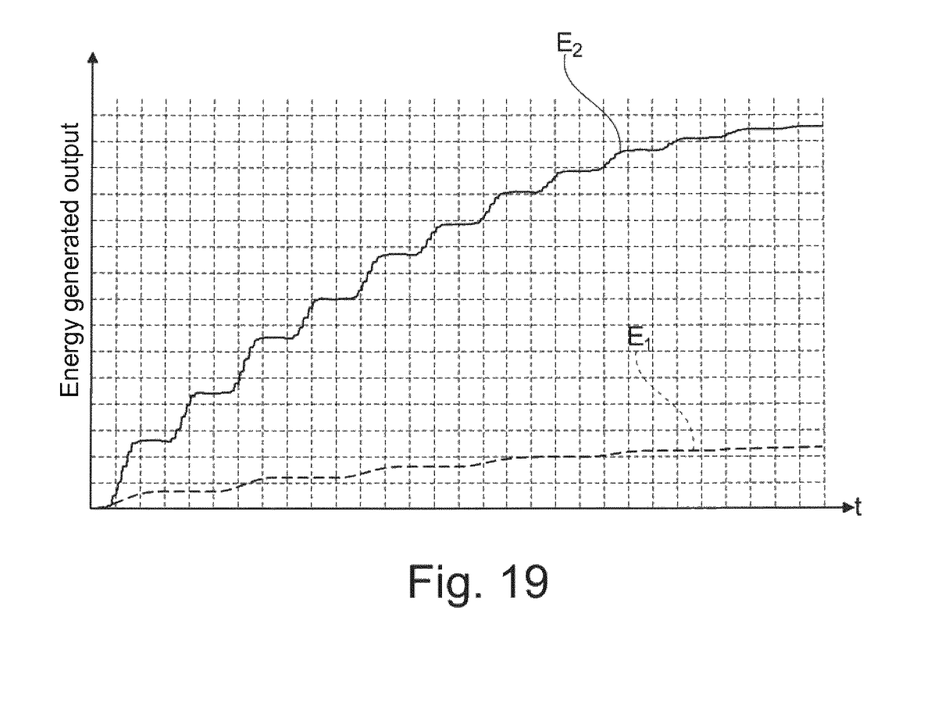
FIG. 19 is a graph showing variations of the output power generated by the structure of FIG. 17, and in comparison the energy generated with a conventional harvesting device.

FIG. 18 illustrates changes over time of the capacitance formed by the combs and counter-combs 82 and 84 of the assembly of FIG. 17. FIG. 19 shows the energy harvested at the output through this capacity variation.

These FIGS. 18 and 19 illustrate the recorded curves for the system of FIG. 17, but these variations of capacity and energy would be similarly obtained with the other structures described in this description.

In FIG. 18, it is seen that the capacity variation includes a sinusoid with decreasing amplitude O superimposed with high frequency variations V. Thanks to the phenomenon of frequency conversion, the variable capacitor will provide a very large number of maxima and minima per unit of time which, for the same stress cycle, will allow, as can be seen in FIG. 19, to harvest a much higher electrical energy $E_2$ than that $E_1$ that would be obtained with a conventional device without frequency conversion.

Figure 20:
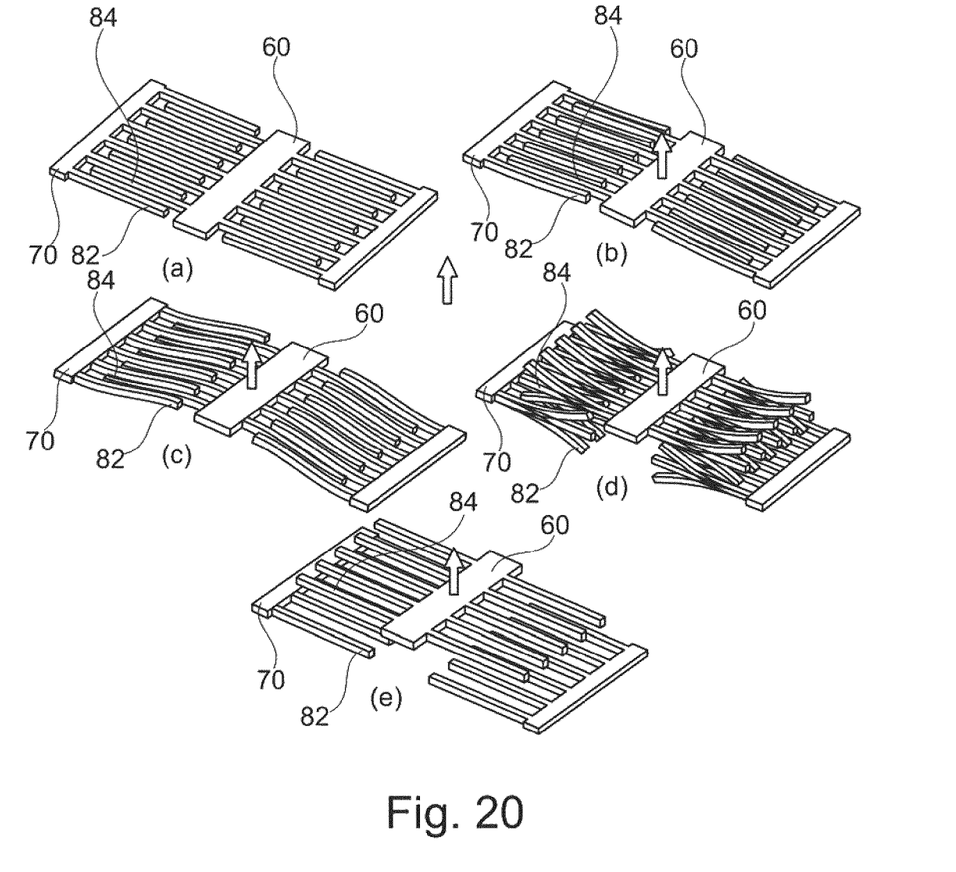
FIG. 20 illustrates another possible implementation of the system of frequency conversion according to the invention, using the deformation of flexible electrostatic fingers under the effect of electrostatic attraction forces.

FIG. 20 discloses an alternative embodiment wherein the electrostatic fingers 82, 84 of the electrostatic structure 80 constitute the resilient deformable element defining the resonant eigenfrequency of the secondary oscillating structure 70. Specifically, the fingers 82, 84 of the combs and counter-combs have geometry such that electrostatic instability phenomena at these fingers occur during movement of the mobile part, thus creating variations in the capacity at high frequencies. The fingers have for this purpose a high aspect ratio, with a thin and elongated shape, thus high flexibility out of the plane allowing vertical electrostatic forces to be significant.

As illustrated by the different states (a) to (e) in FIG. 20, during the vertical displacement of the mobile part 60 the fingers 84 of combs will bend so as to remain facing the fingers 82 of the counter-combs, the combs/counter-combs electrostatic attraction force being strong compared to the mechanical stiffness of the combs. However, when the movement of combs grows, the combs stiffness takes over and the combs are spontaneously released from their electrostatic attraction vis-à-vis the counter-combs. If we superimpose several layers of combs/counter-combs such as those illustrated in FIG. 20, when the combs are released from the attraction of counter-combs of the initial layer, they will enter the field of attraction of counter-combs of the upper layer. This jump from one layer to the other will cause a vibration of high frequency of the combs, causing a change in capacity of the transducer at the same frequency and thereby increasing the number of cycles of charging and discharging of the capacitor, and finally increasing the harvested energy.

Figure 21:
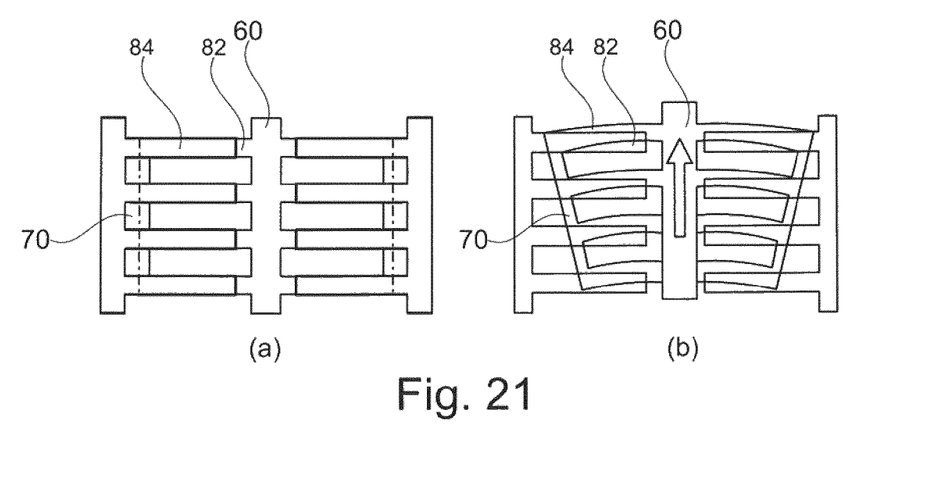
FIG. 21 illustrates a variant of the system of FIG. 20 wherein the ends of the flexible fingers are connected together in order to ensure synchronization of their high-frequency movements.

As shown in FIG. 21, it may be advantageous to couple the ends of the fingers 84 so as to allow a perfect synchronization of their movement on the different layers, and thus of the capacity change collected from each finger.

The invention claimed is:

1. An autonomous intracorporeal capsule, comprising:
a body containing therein electronic circuits and an energy harvester module for supplying power to the electronic circuits;
the energy harvester module comprising a transducer adapted to convert an external physical stress applied to the body of the capsule into electrical energy, wherein the external physical stress results from pressure variations in the environment surrounding the capsule and/or from movements of a wall to which the capsule is anchored;
wherein the energy harvester module further comprises:
a primary oscillating structure being adapted to be moved alternately in one direction and in a second direction at a first frequency;
a secondary oscillating structure coupled to a secondary deformable elastic element and adapted to vibrate at a resonant frequency greater than the first frequency; and
an electrostatic structure comprising a first capacitor electrode coupled to the primary oscillating structure, and a second capacitor electrode coupled to the secondary oscillating structure;
wherein the first and the second electrode are configured to interact so that, under the effect of a movement of the primary oscillating structure into an action area, the first and second electrode operate together, without coming into physical contact, under the effect of an electrostatic attraction force interaction thereby moving the secondary oscillating structure away from its stable equilibrium position causing tensioning of the secondary deformable elastic element, wherein the first electrode comprises a first set of fingers of a first comb structure and the second electrode comprises a second set of fingers of a second comb structure, and wherein the first and second electrode operate together under the effect of the electrostatic attraction force interaction to oscillate between a first configuration in which the first set of fingers and the second set of fingers move toward and are recessed into one another and a second configuration in which the first set of fingers and the second set of fingers retract away from one another;
the secondary oscillating structure being thus driven to a limit at which a tension force exerted by the secondary deformable elastic element caused by the tensioning exceeds the electrostatic attraction force of the electrodes, such that the secondary oscillating structure is released by relaxation effect to vibrate at the resonant frequency; and wherein the transducer is coupled to the secondary oscillating structure, to convert vibration movements thereof at the resonant frequency into electrical energy.

2. The capsule of claim 1, wherein the primary oscillating structure is subjected to the external physical stress.

3. The capsule of claim 2, wherein the secondary oscillating structure is not subjected to the external physical stress.

4. The capsule of claim 1, wherein the first frequency is the frequency of the external stress to which the first oscillating structure is subjected.

5. The capsule of claim 1, wherein the resonant frequency is a natural resonance eigenfrequency.

6. The capsule of claim 1, wherein the electrostatic structure comprises a pair of conversion electrodes forming a capacitor, one of these conversion electrodes being cyclically driven by the secondary oscillating structure, and the electrostatic structure operating by cyclic modification of surfaces opposite one another and/or of the dielectric interval of conversion electrodes with correlative variation in the capacity of the capacitor.

7. The capsule of claim 6, wherein said conversion electrodes include said first and second electrodes of the electrostatic structure.

8. The capsule of claim 1, wherein the transducer is of a piezoelectric type comprising a deformable piezoelectric element configured to be cyclically stressed by the secondary oscillating structure.

9. The capsule of claim 1, wherein the transducer is of an electromagnetic type comprising a mobile magnetic element or a mobile coil configured to be cyclically driven by the secondary oscillating structure.

10. The capsule of claim 1, wherein the primary oscillating structure comprises an inertial mass coupled to the body of the capsule by an elastic suspension adapted to be stressed under the effect of the movements of the capsule in the surrounding medium.

11. The capsule of claim 1, wherein the primary oscillating structure is coupled to a deformable surface out of the body of the capsule and adapted to be stressed under the effect of pressure changes in the medium surrounding the capsule.

12. The capsule of claim 1, wherein the primary oscillating structure and the secondary oscillating structure are coupled to each other by the electrostatic structure.

13. The capsule of claim 12, wherein the secondary oscillating structure is coupled to the body of the capsule by the secondary deformable elastic element.

14. The capsule of claim 1, wherein the primary oscillating structure and the secondary oscillating structure are coupled together by the secondary deformable elastic element.

15. The capsule of claim 1, wherein the fingers of at least one of the first and second electrodes of the electrostatic structure are elastically deformable fingers.

16. The capsule of claim 15, wherein distal ends of elastically deformable fingers of at least one of the first and second electrodes of the electrostatic structure are joined together by a rigid coupling.

17. The capsule of claim 1, wherein the pressure variations in the environment surrounding the capsule and/or from movements of a wall to which the capsule is anchored cause the primary oscillating structure to return to the action area, and wherein the first and the second electrode are configured to repeatedly interact when the primary structure returns to the action area so that the first and second electrode operate repeatedly together under the effect of the electrostatic attraction force interaction thereby moving the secondary oscillating structure away from its stable equilibrium position and causing subsequent release and resonant vibration of the second oscillating structure.

18. An energy harvester module, comprising:
a primary oscillating structure subjected to an external physical stress, the primary oscillating structure being adapted to be moved alternately in one direction and in a second direction;
a secondary oscillating structure not subjected to the external physical stress, the secondary oscillating structure comprising a secondary deformable elastic element and adapted to vibrate at a resonant frequency; and
an electrostatic structure comprising a first capacitor electrode coupled to the primary oscillating structure and a second capacitor electrode coupled to the secondary oscillating structure;
wherein the first and the second electrode are configured to interact so that, under the effect of the external physical stress applied to the primary oscillating structure, the first and second electrode operate together, without coming into physical contact, under the effect of an electrostatic attraction force interaction thereby moving the secondary oscillating structure away from its stable equilibrium position causing tensioning of the secondary deformable elastic element, wherein the first electrode comprises a first set of fingers of a first comb structure and the second electrode comprises a second set of fingers of a second comb structure, and wherein the first and second electrode operate together under the effect of the electrostatic attraction force interaction to oscillate between a first configuration in which the first set of fingers and the second set of fingers move toward and are recessed into one another and a second configuration in which the first set of fingers and the second set of fingers retract away from one another;
the secondary oscillating structure being thus driven to a limit at which a tension force exerted by the elastic deformable element caused by the tensioning exceeds the electrostatic attraction force of the electrodes, such that the secondary oscillating structure is released by relaxation effect to vibrate at the resonant frequency; and
wherein a transducer is coupled to the secondary oscillating structure, to convert vibration movements thereof at the resonant frequency into electrical energy.

19. The energy harvester module of claim 18, wherein the electrostatic structure comprises a pair of conversion electrodes forming a capacitor, one of these conversion electrodes being cyclically driven by the secondary oscillating structure, and the electrostatic structure operating by cyclic modification of surfaces opposite one another and/or of the dielectric interval of conversion electrodes with correlative variation in the capacity of the capacitor.

20. The energy harvester module of claim 18, wherein the primary oscillating structure and the secondary oscillating structure are coupled to each other by the electrostatic structure.

21. The energy harvester module of claim 18, wherein the primary oscillating structure and the secondary oscillating structure are coupled together by the secondary deformable elastic element.

* * * * *